(12) United States Patent
Newman

(10) Patent No.: US 10,016,597 B2
(45) Date of Patent: Jul. 10, 2018

(54) ELECTROSTATIC GROUNDING APPARATUS FOR ELECTRICALLY GROUNDING A MAT HAVING AN ELECTRICALLY CONDUCTIVE LAYER

(71) Applicant: Scott Newman, Beaverton, OR (US)

(72) Inventor: Scott Newman, Beaverton, OR (US)

(*) Notice: Subject to any disclaimer, the term of this patent is extended or adjusted under 35 U.S.C. 154(b) by 273 days.

(21) Appl. No.: 14/879,128

(22) Filed: Oct. 9, 2015

(65) Prior Publication Data
US 2016/0105946 A1    Apr. 14, 2016

Related U.S. Application Data

(60) Provisional application No. 62/062,971, filed on Oct. 13, 2014.

(51) Int. Cl.
| | | |
|---|---|---|
| *H05F 3/02* | (2006.01) | |
| *A61N 1/14* | (2006.01) | |
| *G01R 29/12* | (2006.01) | |
| *G01R 27/18* | (2006.01) | |

(52) U.S. Cl.
CPC .......... *A61N 1/14* (2013.01); *G01R 27/18* (2013.01); *G01R 29/12* (2013.01); *H05F 3/02* (2013.01); *H05F 3/025* (2013.01)

(58) Field of Classification Search
CPC .......... H01R 13/65802; H01R 13/28; H01R 23/6873; H01R 25/006; H01R 13/648; H01R 24/50; H01R 13/6485; H01R 4/64; H01R 24/40; H01R 12/716; H01R 9/032; H01R 13/652; H01R 4/2429; H01R 4/2495; H05F 3/02; H05F 3/025; H05F 3/00; H05F 3/04; G02B 6/4277; A61N 1/14; H05K 9/0067; H01L 23/60; G01R 27/18; G01R 31/025; G01R 27/14; G01R 29/12; G01R 31/001; G01R 31/026; G08B 3/10; A47B 21/00
See application file for complete search history.

(56) References Cited

U.S. PATENT DOCUMENTS

| | | | |
|---|---|---|---|
| 4,012,578 A | | 3/1977 | Moran et al. |
| 4,215,306 A | | 7/1980 | Mace |
| 4,459,633 A | * | 7/1984 | Vandermark ............ A61N 1/14 |
| | | | 361/212 |
| 4,569,445 A | | 2/1986 | Kovats et al. |
| 5,585,730 A | | 12/1996 | Pazda et al. |
| 5,760,589 A | | 6/1998 | Katsuie |
| 6,106,310 A | | 8/2000 | Davis et al. |
| 6,166,550 A | | 12/2000 | Abramsohn et al. |

(Continued)

*Primary Examiner* — Thienvu Tran
*Assistant Examiner* — Nicolas Bellido
(74) *Attorney, Agent, or Firm* — Hancock Hughey LLP

(57) ABSTRACT

An ESD grounding apparatus for grounding mats or other equipment to provide a ground connection to mat as well as receptacles for operator wrist straps, and other equipment. The apparatus attaches to a mat by means of securing member such as a clamp or compressing screw rather than using destructive rivets or snaps that create holes in the mat. By using a securing member to secure the device to the mat, the device can be easily removed and reused in another location without damaging or weakening the mat, whereas the previous devices require installing an additional snap into the mat in each location that requires a ground.

18 Claims, 11 Drawing Sheets

(56) References Cited

U.S. PATENT DOCUMENTS

| | | | |
|---|---|---|---|
| 6,223,088 B1* | 4/2001 | Scharnberg | A61N 1/046 439/909 |
| 6,304,457 B1 | 10/2001 | Liu et al. | |
| 6,475,038 B1* | 11/2002 | Franck | H01R 4/363 439/811 |
| 6,628,122 B2 | 9/2003 | Newman | |
| 6,974,935 B2* | 12/2005 | O'Grady | C08K 3/04 219/541 |
| 6,986,673 B2 | 1/2006 | de la Borbolla | |
| 7,456,356 B2 | 11/2008 | Newman | |
| 2004/0154818 A1* | 8/2004 | Franks, Jr. | H01R 4/643 174/51 |
| 2009/0126169 A1* | 5/2009 | Nielsen | A47F 3/12 24/486 |

\* cited by examiner

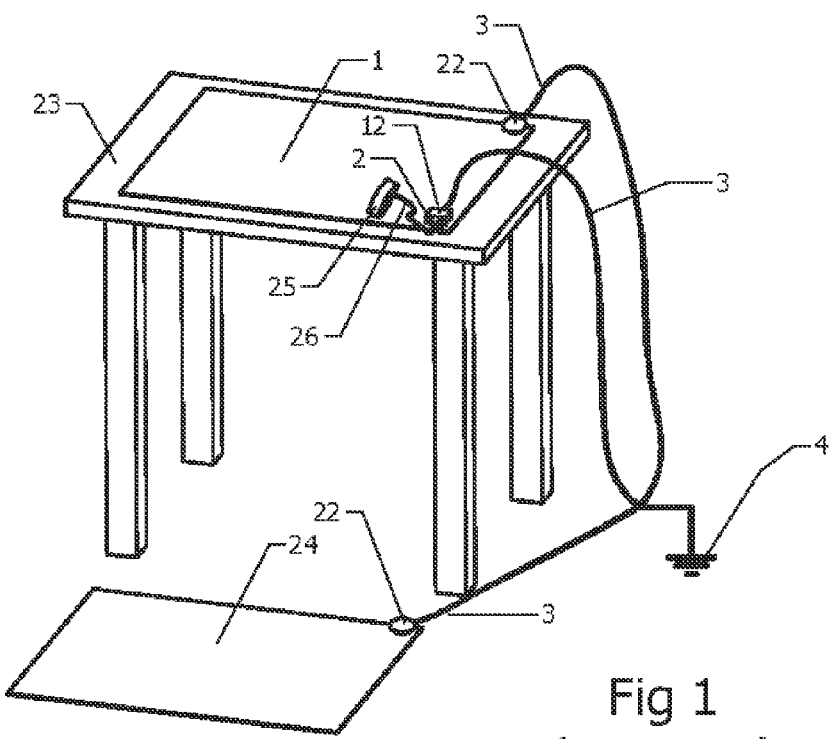
Fig 1
(Prior Art)
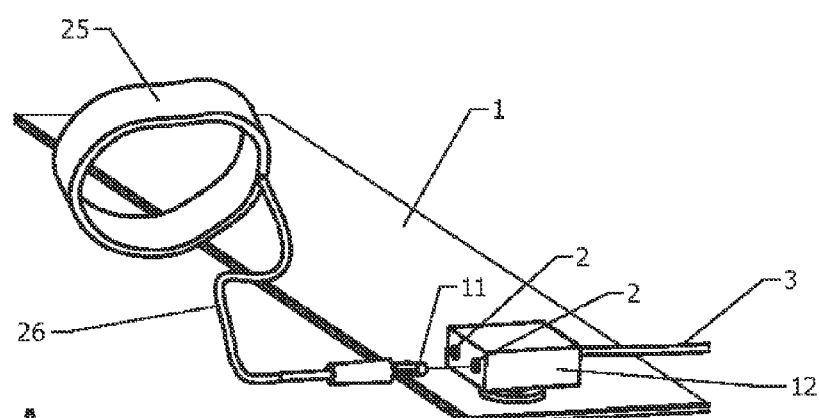
Fig 1-A
(Prior Art)

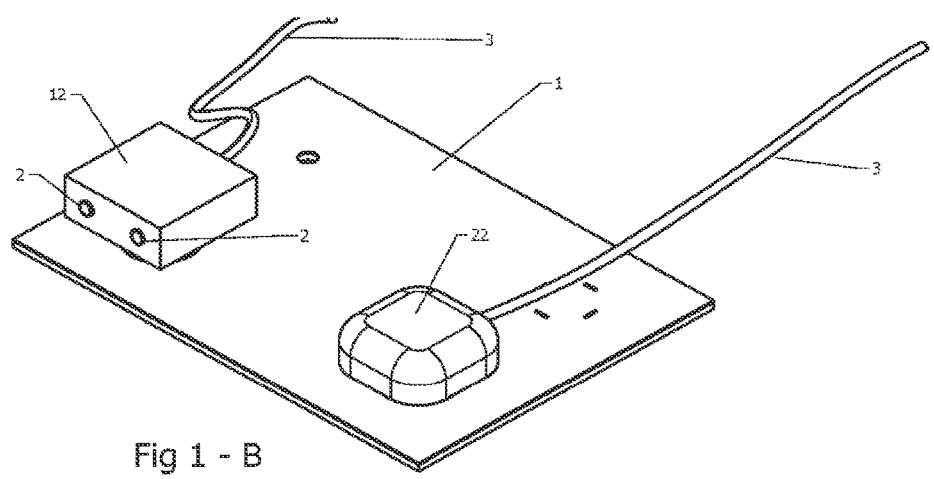
Fig 1 - B
(Prior Art)
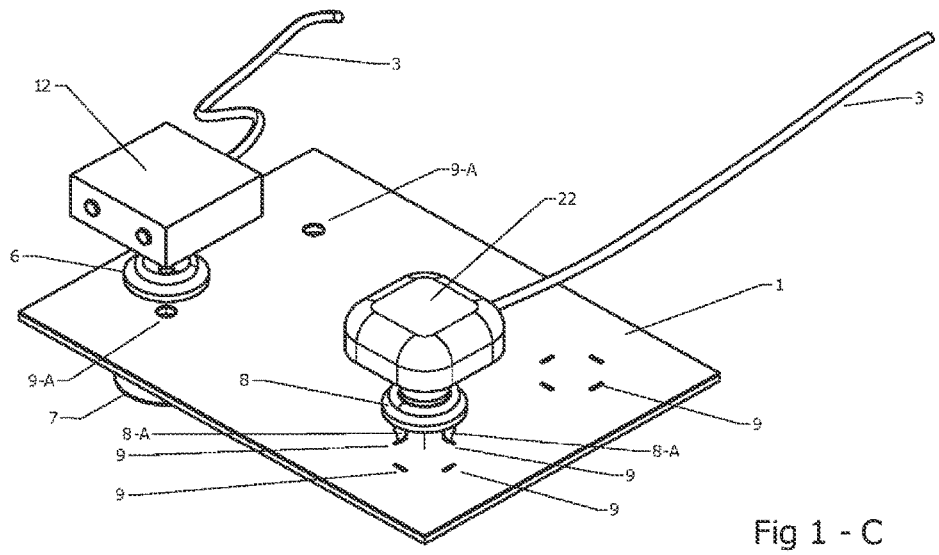
Fig 1 - C
(Prior Art)
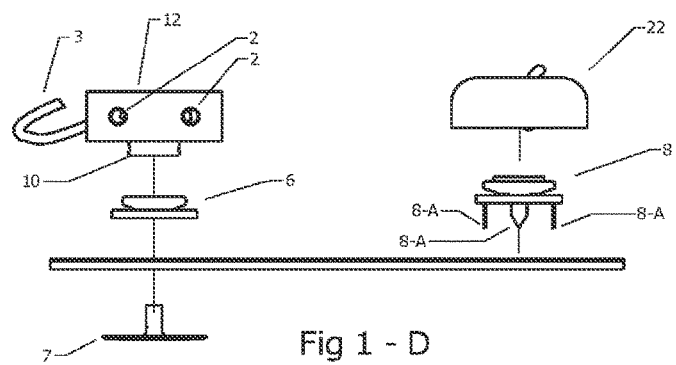
Fig 1 - D
(Prior Art)

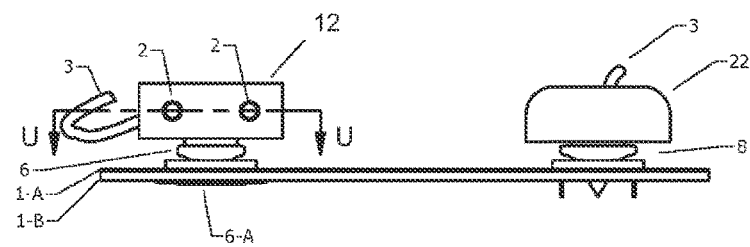
Fig 1-E (Prior Art)
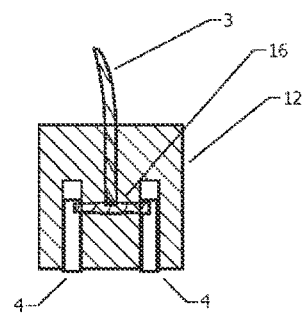
Fig 1-F (Prior Art)
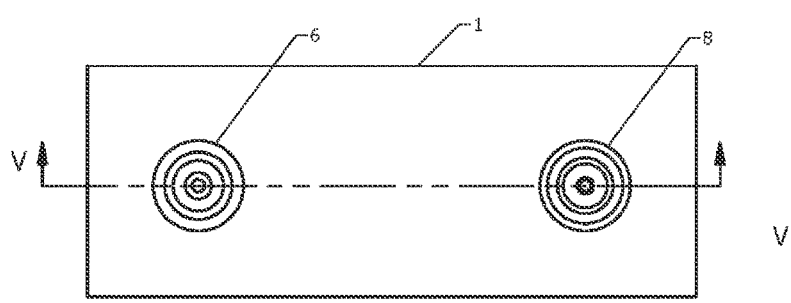
Fig 1-G (Prior Art)
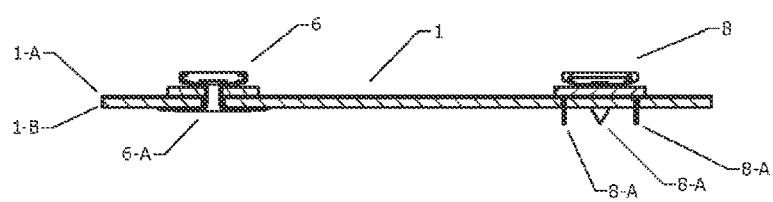
Fig 1-H (Prior Art)

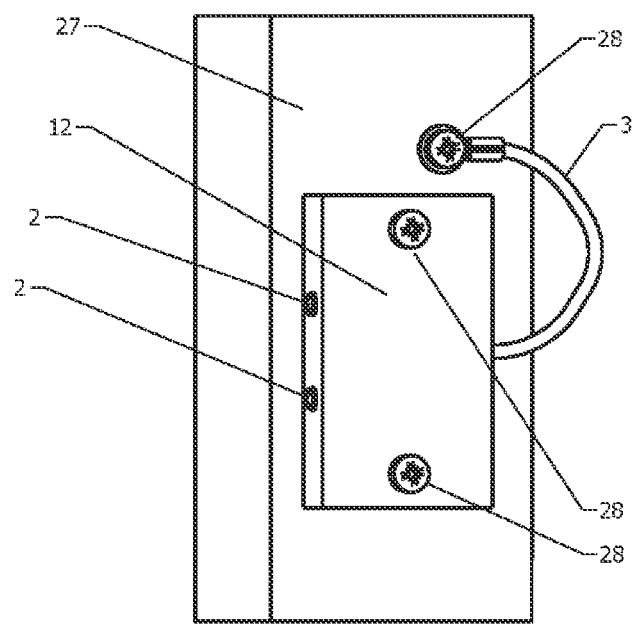
Fig 1-I (Prior Art)

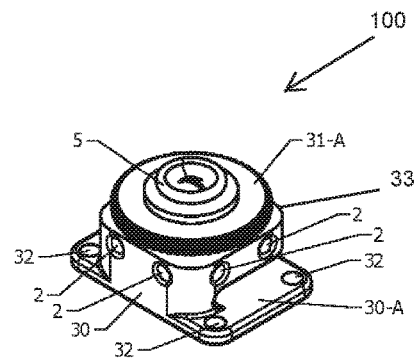
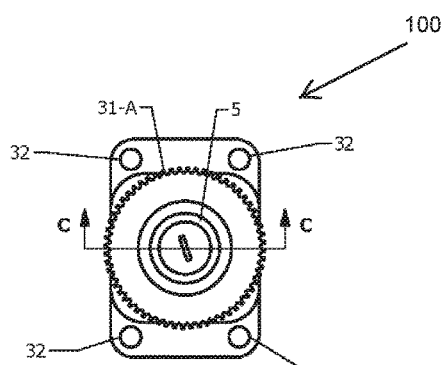
Fig 2                Fig 2 - A
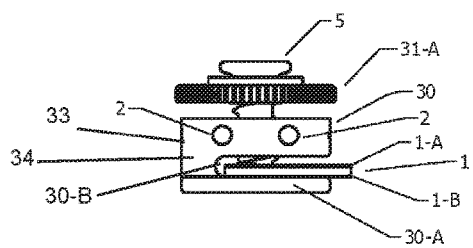
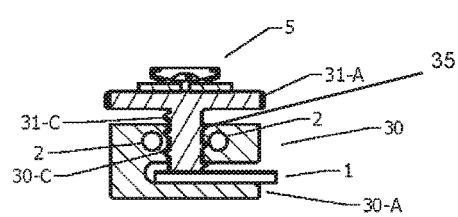
Fig 2 - B            Fig 2 - C
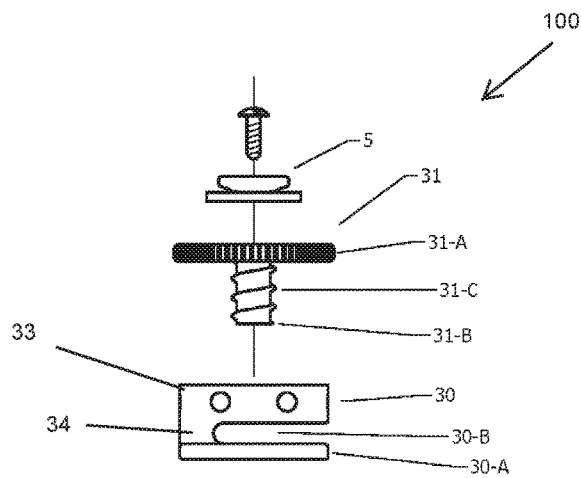
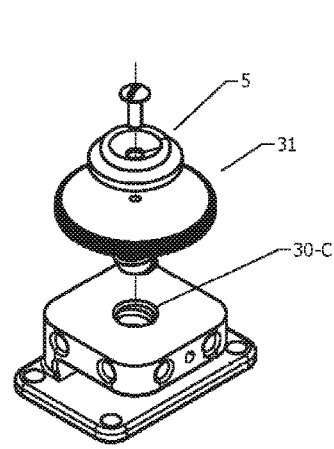
Fig 2 - D            Fig 2 - E

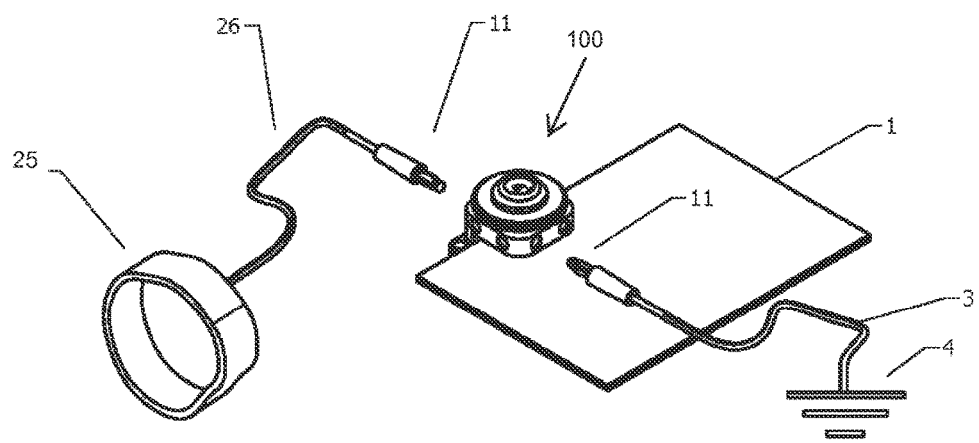
Fig 2 - F
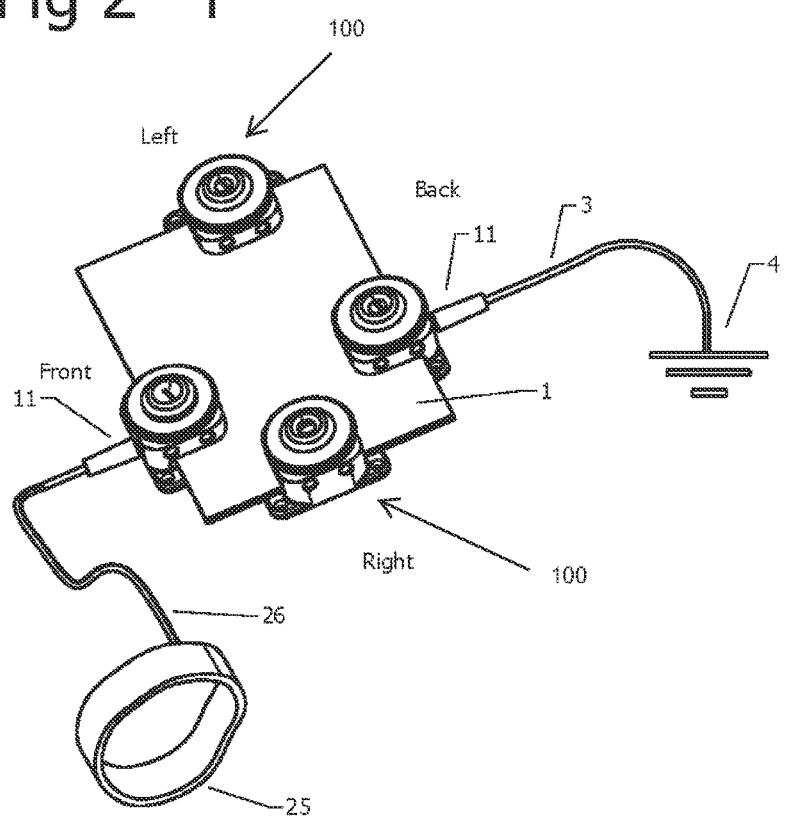
Fig 2 - G

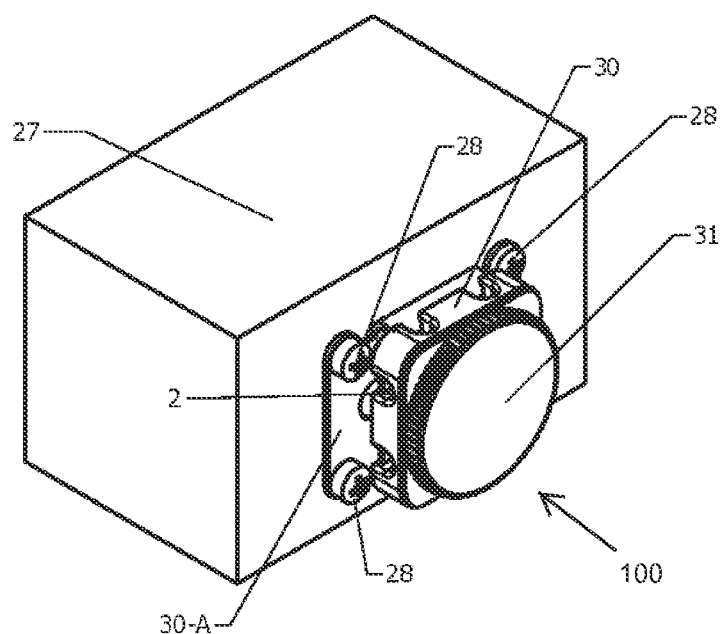
Fig 2 - H

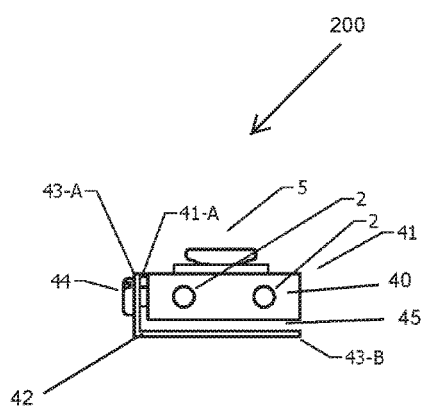
Fig 3
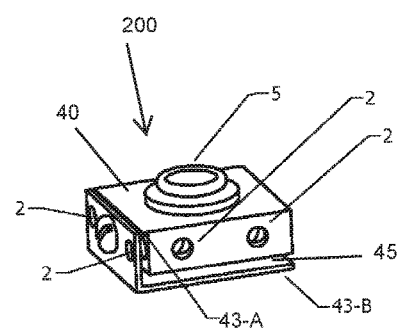
Fig 3-A
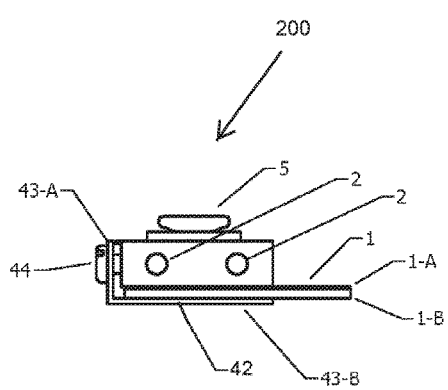
Fig 3-B
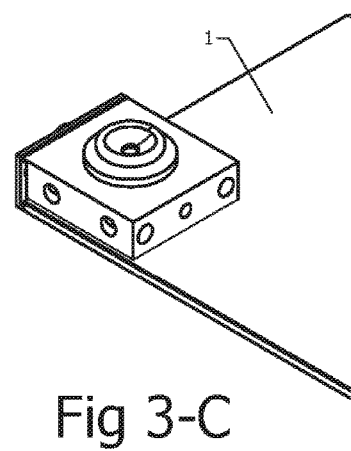
Fig 3-C

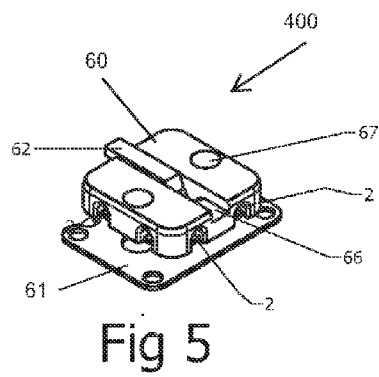
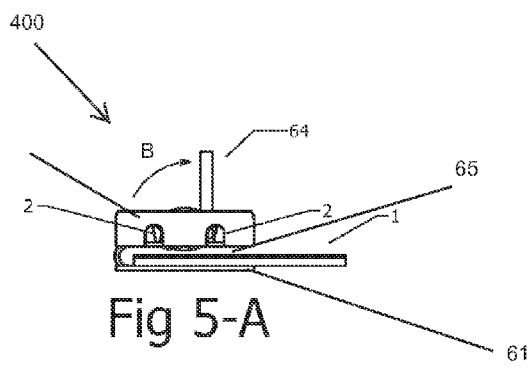
Fig 5
Fig 5-A
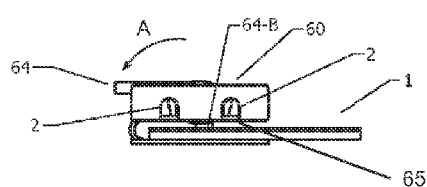
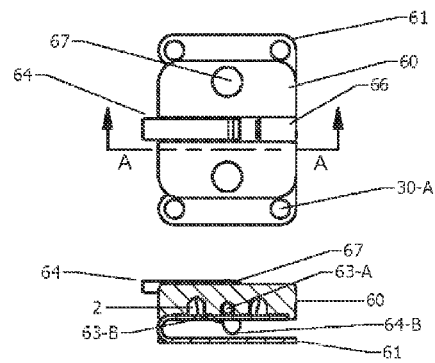
Fig 5-B
Fig 5-C
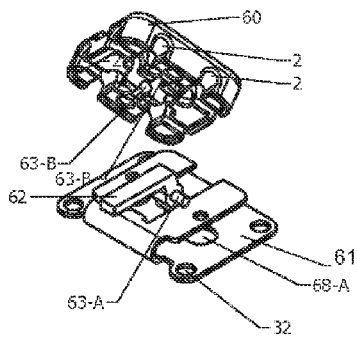
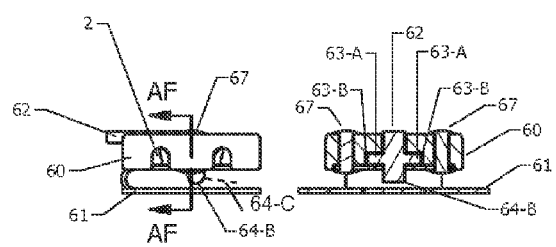
Fig 5-D
Fig 5-E

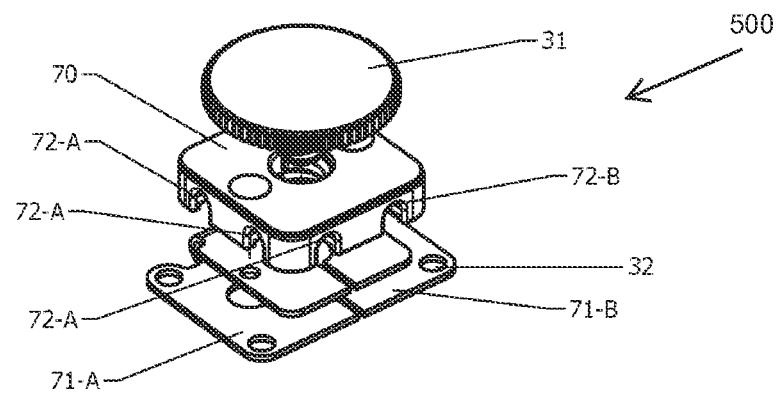
Fig 6-A
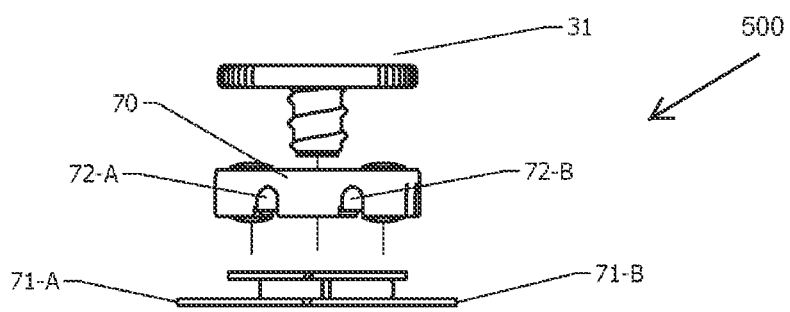
Fig 6-B
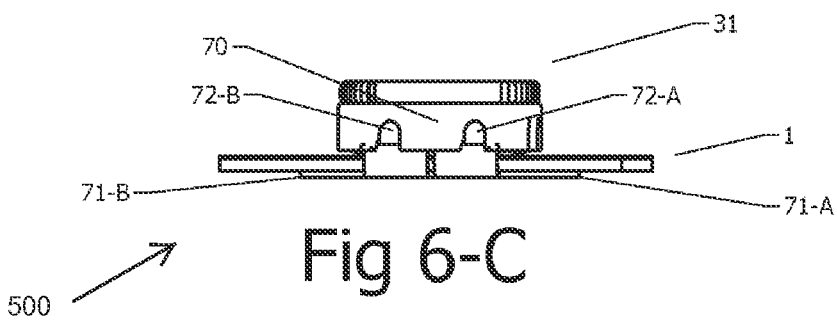
Fig 6-C

ELECTROSTATIC GROUNDING APPARATUS FOR ELECTRICALLY GROUNDING A MAT HAVING AN ELECTRICALLY CONDUCTIVE LAYER

TECHNICAL FIELD

This invention relates to electrostatic discharge (ESD) and apparatus and techniques for minimizing or eliminating ESD, and more specifically, apparatus for use in the grounding of benches, ESD bench mats, carts, shelving, and other equipment to reduce the risks from ESD.

BACKGROUND

Static electricity is commonly defined as an electrical charge resulting from the imbalance of electrons on the surface of a material. Most people are quite familiar with the everyday effects of static electricity—it is the shock one receives when touching a doorknob after walking across a carpet. The technical name for the electrical shock just described is electrostatic discharge. ESD is technically described as the transfer of electrical charge between bodies—for instance, a human hand and a doorknob—that are at different electrical potentials.

In most everyday situations, ESD can be a bother but rarely a problem. However, the problems resulting from ESD are magnified in industrial settings, where ESD is a major concern. Among the many problems that static discharge can cause are the unintentional ignition of flammable materials, damage to electronic components and systems, and the attraction of contaminants such as charged dust particles in clean room environments. Even centuries ago military forces were aware that ESD could cause the unintentional ignition of black powder. To alleviate this sometimes-catastrophic problem, ESD control measures were used as early as the 14th century to protect black powder stores. Today, many industries—from high tech manufacturing plants to businesses commonly thought of as "smoke stack" industries—are concerned with ESD and its control, since controlling ESD can lead to a safer work environment and reduction or elimination of damage resulting from ESD.

While nearly all industries are or should be concerned with controlling ESD, the concern is most acutely felt by businesses in the electronics industry. To give just a few examples of the damage that ESD can cause in the electronics industry, it can destroy or degrade semiconductor devices by changing operational characteristics. It can cause disruptions to the normal operation of an electronic system—sometimes leading to equipment failure, and in clean rooms it can cause charged particles to adhere tightly to the surface of a silicon wafer, resulting in distinct problems with wafer production and efficiency.

Given these problems and the economic damage that can result from them, control of ESD is a major concern and a complete industry has grown up around the field of ESD control.

A critical component of an ESD control program is dissipating and neutralizing ESD during handling, transporting and storing of ESD sensitive materials.

Some very common ESD protective measures are to use conductive floors, benches, bench and floor mats, wrist straps, containers, storage shelves, and transport carts all connected to a common electrical ground to reduce any build-up of electrical potential between objects or people, thereby reducing the risk of an ESD event. In addition, there are several known ESD grounding devices that are commonly used—some of these are described below and shown in the drawings.

SUMMARY OF THE INVENTION

The present invention defines an apparatus for eliminating the risks of ESD. The inventive apparatus easily installs onto an ESD mat, a workbench, or equipment, to provide an ESD ground for the device as well as ground plugs to ground operators or other devices. Unlike prior art ESD mat grounding devices that require drilling or cutting holes to install an attachment snap, the invention attaches directly to the mat without damaging the mat and can quickly and easily be moved to a new location without causing damage to the mat.

The present invention also includes multiple receptacles to attach ground wires and banana plugs and built-in mounting holes as a means to attach to equipment, on or under a workbench or onto nearly any location that requires a ground. If attached to a grounded mat or equipment frame, the present invention can use the mat or equipment ground to provide a grounding point for other devices such as wrist straps or other equipment. Additionally, if the present invention is connected to ground with a grounding wire, it can ground an ungrounded mat or equipment frame as well as provide wrist strap grounds for operators or grounds for other equipment.

Objects and Advantages

Several objects and advantages of the invention described herein and shown in the drawings include but are not limited to:

Installs onto an ESD mat without the use of tools
Easy to relocate on a mat because no snaps are required
Infinitely adjustable on a mat because no mounting holes are required in the mat to install a snap
Mounts directly to the mat rather than to a mounting snap, so it is held securely at the same angle
Receptacles are accessible from multiple directions
Does not damage an ESD mat
Easier to install because no mounting snaps or holes are required
Connects directly to an ESD mat, so it does not suffer from intermittent electrical contact between the male and female part of the snap or from gaps between parts of the snap itself
Ground wire is optional rather than permanently attached
Ground wire is replaceable if damaged, unlike prior art
Ground wire can be mounted in a plurality of directions
Ground connection can be attached to this device by means of plugging a banana plug attached with a ground wire into one of the receptacles or by means of a attaching a ground wire with a screw or other fastener directly to the device.

Other objects and advantages of the invention will be evident upon review of the description and drawings. These include:

A. An ESD grounding apparatus for establishing an electrical pathway from a base that is in electrical contact with a mat to an adaptor for attaching a grounding wire;

B. An ESD grounding apparatus for establishing an electrical pathway from a base that is in electrical contact with a mat to an adaptor for attaching a grounding wire without damaging the integrity of the mat;

C. An ESD grounding apparatus that may be attached to a mat for establishing an electrical pathway from the apparatus to a conductive layer in the mat and for attaching a grounding wire to the apparatus to thereby ground the mat.

D. An ESD grounding apparatus wherein a conductive member makes electrical contact with an electrically conductive layer in the mat and the conductive member includes an electrical connection for attaching a grounding wire to thereby ground the mat.

BRIEF DESCRIPTION OF THE DRAWINGS

The invention will be better understood and its numerous objects and advantages will be apparent by reference to the following detailed description of the invention when taken in conjunction with the following drawings in which the series of drawings FIG. 1 through FIG. 1I illustrate known prior art, and in which various embodiments of the present invention are shown in the series of FIGS. 2 through 6.

Figure 4:
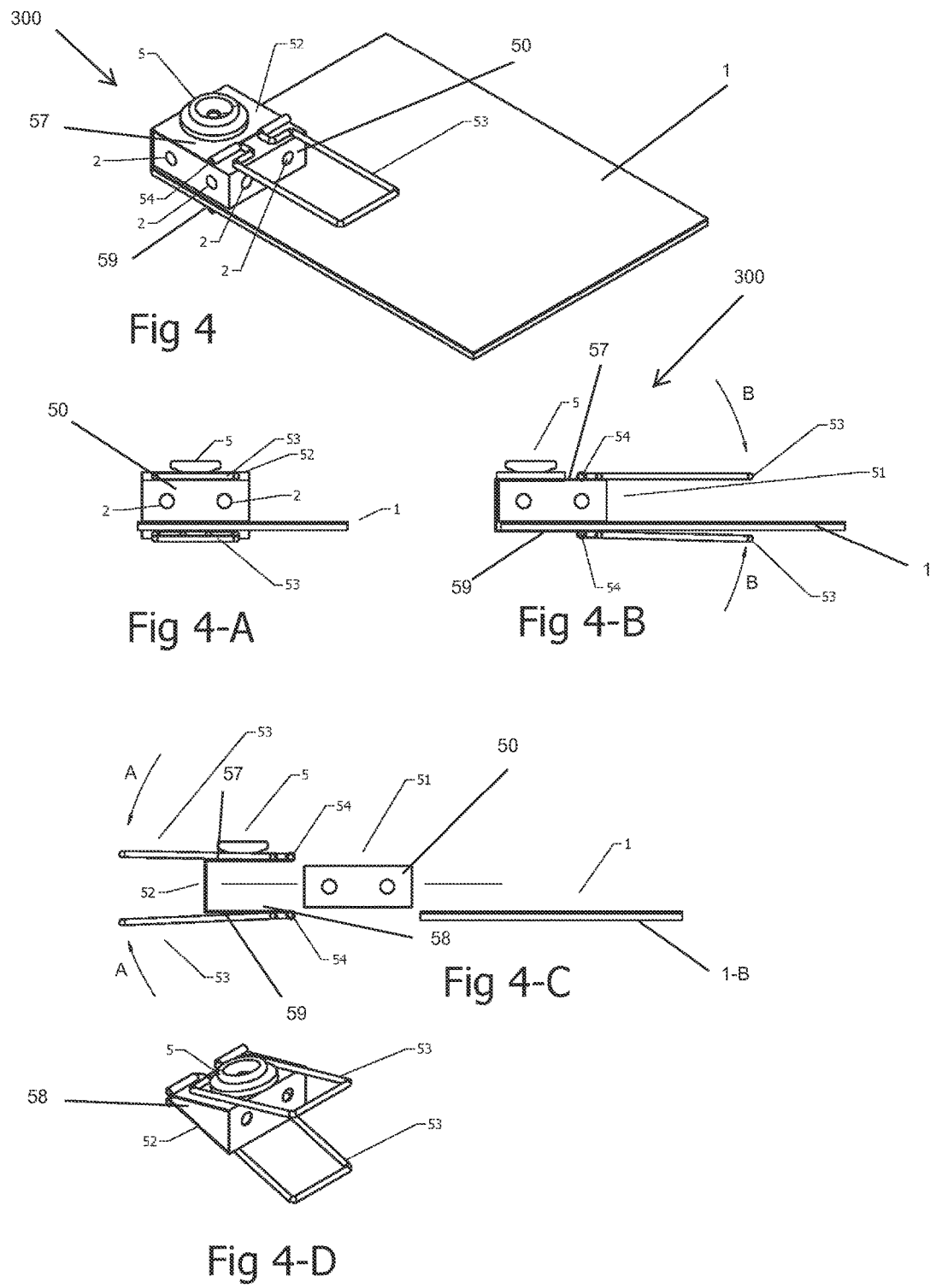

Various elements of prior art devices are shown in FIG. 1 through FIG. 1I;

FIG. 1 is a perspective view of a typical ESD-safe workbench according to the prior art;

FIG. 1-A is a perspective view of a typical ESD mat with grounding devices 11 and 22 attached;

FIG. 1-B is a perspective view of an ESD mat with a mat ground with receptacles 12 and mat ground only 22;

FIG. 1-C is a perspective partial exploded view of an ESD mat with a mat ground with receptacles and mat ground only;

FIG. 1-D is a front partial exploded view of an ESD mat 1 with a mat ground with receptacles 12 and mat ground only 22;

FIG. 1-E is a front view of an ESD mat with a mat ground with receptacles and mat ground only;

FIG. 1-F is a cross sectional view of a mat ground with receptacles of the type shown in FIG. 1-E and taken along the line E U-U of FIG. 1-E;

FIG. 1-G is a top view of an ESD mat with mounting snaps installed;

FIG. 1-H is a cross sectional view of the ESD mat 1 from FIG. 1-G taken along the line V-V of FIG. 1-G, showing a female snap rivet style 6 and a female snap prong style 8 installed into the ESD mat 1 with the bottom side of the rivet 6-A and the prongs 8-A protruding through the less conductive mat Top 1-A layer and the highly conductive mat Bottom 1-B Layer of the two layer ESD mat 1 and making electrical connection with the highly conductive bottom side 1-B of the ESD mat 1;

FIG. 1-I is a perspective view of a mat ground installed onto a grounded conductive metal frame 27 with a ground wire 3 and screw 28 to provide an electrical ground from said frame 27;

Illustrated embodiments of the present invention are shown in FIGS. 2 through 6:

FIG. 2 is a perspective view of the a first illustrated and preferred embodiment of an ESD grounding device according to the present invention, with receptacles for attaching electrical cords to the apparatus;

FIG. 2-A is a top view of the embodiment shown in FIG. 2;

FIG. 2-B is a right view of the embodiment shown in FIG. 2 installed onto an ESD mat;

FIG. 2-C is a right cross sectional view of the embodiment shown in FIG. 2, taken along the line C-C of FIG. 2-A, and installed onto an ESD mat;

FIG. 2-D is a right exploded view of the embodiment shown in FIG. 2;

FIG. 2-E is an exploded perspective view of the embodiment of FIG. 2;

FIG. 2-F is a partially exploded view of the ESD apparatus shown in FIG. 2 installed on an ESD mat showing how an ESD wrist strap 25 and a wrist strap grounding wire 26 can be attached by means of the banana jack 11;

FIG. 2-G is a perspective view of four ESD units according to the embodiment of FIG. 2 installed onto all four sides of an ESD mat with one unit connected to an ESD wrist strap, a second unit connected to a ground cable, and two units connected only to the mat;

FIG. 2-H is a perspective view of the embodiment shown in FIG. 2 installed onto a conductive metal frame 27 and achieving electrical connection to the frame by attaching screws 28 through the conductive base 30-A;

FIG. 3 is a right side view of a second illustrated embodiment of an ESD grounding apparatus according to the present invention;

FIG. 3-A is a perspective view of the embodiment of FIG. 3;

FIG. 3-B is a right view of the second illustrated embodiment of FIG. 3 installed onto an ESD mat;

FIG. 3-C is a perspective view of the second illustrated embodiment installed onto an ESD mat;

FIG. 4 is a perspective view of a third alternative and illustrated embodiment of an ESD grounding apparatus according to the invention installed onto an ESD mat;

FIG. 4-A is a rear view of embodiment of FIG. 4 installed on an ESD mat with handles 53 in the relaxed position;

FIG. 4-B is a side view of embodiment of FIG. 4 installed on an ESD mat with handles 53 in the relaxed position;

FIG. 4-C is a partially exploded right view of the embodiment of FIG. 4 showing how it would be installed on an ESD mat with handles 53 opening the spring clamp 52;

FIG. 4-D is a partial perspective view of spring clamp 52 of the embodiment of FIG. 4 with the spring clamp 52 in the relaxed position;

FIG. 5 is a perspective view of yet another illustrated embodiment of an ESD grounding device according to the invention;

FIG. 5-A shows the embodiment of FIG. 5 with the actuating lever 62 in the open position to enable it to accept or remove to an ESD mat 1;

FIG. 5-B shows the embodiment of FIG. 5 with the actuating lever 62 in the closed position to enable it to clamp to an ESD mat 1;

FIG. 5-C is two juxtaposed views that show a top view of the embodiment of FIG. 5, and beneath it, a right side cross sectional view taken along the line A-A of the top view of the embodiment of FIG. 5 with the actuating lever 62 in the closed position;

FIG. 5-D shows a right-rear partially exploded perspective view of the embodiment of FIG. 5;

FIG. 5-E is two juxtaposed views that on the left is a side elevation view of the embodiment of FIG. 5, and on the right is a cross sectional view taken along the line AF-AF of the elevation view;

FIG. 6-A shows a partially exploded perspective view of the yet another embodiment of an ESD grounding device according to the invention;

FIG. 6-B shows a partially exploded front view of the embodiment of FIG. 6;

FIG. 6-C is a back view of the embodiment of FIG. 5 installed on a mat.

DETAILED DESCRIPTION OF ILLUSTRATED EMBODIMENTS

Prior to describing the present invention in detail the known prior art will be described in order to provide some measure of background. In the figures like structures are often identified with the same reference numbers.

Common types of ESD grounding used for work benches, floors, and people in the electronics, laboratories, and other industries are shown in FIG. 1 through FIG. 1-I. Two common types of known conventional ESD grounding devices are shown in FIG. 1-A through 1-I. One type is for a ground only 22 and is used for grounding of ESD mats 1 or ESD floor mats 24. The second type of a prior art ESD grounding device is a mat ground with receptacles 12, which is used for grounding ESD mats 1 and includes receptacles 2 for grounding personnel or equipment. Variations of the mat ground with receptacles 12 sometimes include mounting holes 32 for attaching to a frame 27 with screws 28 as shown in FIG. 1-I. Prior art mat grounds 12 can provide a ground derived from a grounded conductive frame 27 as shown in FIG. 1-I, but are not designed to provide grounding for an ungrounded frame 27 without installing an external ground wire (not shown) or installing an attachment snap (not shown) onto the equipment.

Conventional ESD mat grounding devices are illustrated in FIG. 1-A to 1-H, and consist of devices such as the unit shown in FIG. 1-D that have a male snap 10 located on the bottom of the device, which is mounted to a mat 1 by means of a female snap 6 or 8 that has been attached to an ESD mat 1 by means of rivets 7, prongs 8-A, or the like, such as those in FIG. 1-D.

FIG. 1-F is a section view that shows the typical construction of a known prior art device 12 in which an electrically conductive element 16 connects the receptacles 2, the male snap 10 (not shown in this view) and the ground wire 3, all of which are encased in an insulated housing of the main body 12.

Work benches 23, bench ESD mats 1, floor ESD mats 24, equipment, and the like such as those in FIG. 1 and FIG. 1-A are typically connected to a common ground 4 such as an electrical or building ground. While the conventional mat grounding devices, shown in the prior art, generally provide a ground for a mat 1 and operator wrist strap, they are difficult to install, difficult to move, the installation damages the mat, and do not provide a reliable ground to a mat because of intermittent connections within and between the many parts of the snaps that are used to connect to a mat, and require additional grounding wires to be added to ground equipment frames.

It is common practice in manufacturing, engineering and lab settings to create flexible workstations that can be easily reconfigured to accommodate different products, tests, or other needs.

Although the prior art mat grounding devices can be removed by un-snapping them from the female snap attached to the mat, there are two problems that are created. The first is that the female snap that remains on the mat is frequently in the way and does not allow items to lie flat on the mat. Placing a heavy item, such as a tester or computer, on top of the snap often damages the snap to the point that it requires replacement, which typically a new hole or several slots to be cut into the mat. Each new hole damages the mat by creating a weak spot in the mat, and it is common to see mats with corners torn or missing. The second problem caused by removing the grounding device is that the mat still requires a ground to be attached in a new location. As a result, yet another grounding snap must be installed, thereby creating more holes in the mat.

The present invention will now be described in detail with reference to the drawings of FIGS. 2 through 6. It will be understood that relative directional terms may be used at times to describe components of the invention and relative positions of the parts. As a naming convention, the plane of the floor in a living or work space, or the plane of the working surface of a work bench that is oriented parallel to a horizontal floor is considered to be a generally horizontal surface. Other relative directional terms correspond to this convention: "upper" refers to the direction above and away from the ground plane; "lower" is generally in the opposite direction, "inward" is the direction from the exterior toward the interior of the adaptor, "vertical" is the direction normal to the horizontal ground plane, and so on.

Preferred and illustrated embodiment of an ESD grounding apparatus 100 according to the invention shown in FIGS. 2 through 6. A first preferred embodiment of the grounding apparatus 100 is shown in FIGS. 2 through 2-H. The body 30 of grounding apparatus 100 may be constructed from any sufficiently strong and resilient conductive material such as carbon loaded ABS, nylon, zinc, or most any conductive material. Optionally, grounding apparatus 100 can be made with an insulating material that is either coated with conductive material or has conductive material inserted to make the required connections. A material with a resistance of less than 20,000 ohms-cm is desirable.

Apparatus 100 comprises a main body 30 and a base 30-A. A slot 30-B is defined in main body 30 between the base 30-A and the upper body section 33 of the main body 30. More specifically, as best seen in FIG. 2-B and slot 30-B is defined between the base 30-A and the upper body section 33 by body section 34 that is less wide than the rest of the upper body section 33. As detailed below, slot 30-B defines a mat 1 receiving receptacle.

Although the entire apparatus 100 may be electrically conductive, the areas that are required to be conductive would be from each of the receptacles 2 to the base 30-A to define an electrically conductive path from the receptacles to the base. The entire apparatus 100 may be fabricated in a mono-lithic, unitary piece or may be fabricated in separate pieces that are attached to one another with appropriate fasteners or adhesives. For instance, the base 30-A may be fabricated as a first piece and the upper body section 33 may be fabricated as a second piece (which in side elevation would be L-shaped). The base 30-A would be directly attached to the upper body section in the orientation shown in, for example, FIG. 2-B, either with fasteners or adhesives, etc., and in any case, to insure electrical connectivity through the two pieces. Optionally, a conventional snap 5 may be included with the embodiment shown in FIG. 2. The snap 5 is electrically connected to the base 30-A. Moreover, the main body 30 and the tensioning screw 31 would require conductive material, coating, or inserts as well.

The main body 30 is shown with two receptacles 2 on each side of the four-sided body, each receptacle 2 sized appropriately for banana plugs 11 (e.g., FIG. 2-F). Slot 30-B, as shown in FIG. 2-D, is used to receive the edge portion of a mat 1 so that the mat is in the slot 30-B between the upper body section 33 and the base 30-A. A threaded bore 30-C extends through the upper body section 33 from the upper surface 35 thereof and into the portion of the body section overlying slot 30-B so that the bore 30-C extends into slot 30-B. A tensioning screw 31 is threaded into threaded bore 30-C from the top down as shown in FIGS. 2-D, 2-C and 2-E. With a mat 1 received in slot 30-B the tensioning screw 31, which has external threads 31-C, tightened so that its tip 31-B bears down against mat 1 to thereby capture, secure and clamp the mat 1 between the tip 31-B of the tensioning screw 31 and the base 30-A, and to establish an electrically conductive pathway from the mat 1 through apparatus 100 to receptacles 2.

The bottom layer 1-B of mat 1 is highly conductive. Tensioning screw 31 is effective to clamp the mat and with its highly conductive bottom layer 1-B against the base 30-A and thereby provides a low resistance electrical connection between the bottom layer 1-B of the mat and the base 30-A. Since the base 30-A is electrically connected to the receptacles 2 in the body 30, the base 30-A, the bottom layer 1-B, and the receptacles are electrically connected.

In addition to attaching to an ESD mat 1, auxiliary mounting holes 32 in the base 30-A also provide means to secure the apparatus 100 to nearly any surface or equipment as in FIG. 2-H. Because the Base 30-A is electrically conductive and electrically connected to receptacles 2, apparatus 100 may be grounded by attaching it to a grounded conductive frame 27 of a piece of equipment such as shown in FIG. 2-H. Alternately, with the connection of a grounding wire 3 to apparatus 100, the apparatus can provide a ground to a piece of equipment 27.

Operation of the Embodiment of FIG. 2

Apparatus 100 is attached to a mat 1 with the edge of the mat in slot 30-B as described above and as shown in the drawings, especially FIG. 2-F. The tensioning screw 31 is tightened to secure apparatus 100 to mat 1 and to ensure an electrical connection from the mat to apparatus 100. To ground the assembly a ground wire 3 with a banana plug 11 on one end is plugged into a receptacle 2. The other end of ground wire 3 is attached to common, electrical, or building ground 4. Alternately, a ground wire 3 can also be installed without the use of a banana jack 11 by installing one end of the ground wire 3 into one of the receptacles 2 and securing the wire to the main body 30 with a fastener, such as a screw. The fastener can be installed in the same receptacle 2 as the wire 3, or into the closest receptacle 2 at a 90 degree angle from the receptacle 2 that contains the ground wire 3.

To ground apparatus 100 by means of a grounded ESD mat 1, attach the apparatus to a grounded mat as shown In FIG. 2-G, right and left side.

To ground the apparatus 100 by means of a ground wire 3, attach a ground wire 3 by means of banana plug 11 and attach the other end of ground wire 3 to common, electrical, or building ground 4 as shown In FIG. 2-F.

To ground a mat 1 using the apparatus 100, install a grounded apparatus 100 onto any edge of a mat 1 as shown In FIG. 2-F, back.

To ground an ungrounded conductive material or equipment frame 27 such as in FIG. 2-H using the apparatus 100, attach a grounded apparatus to the ungrounded conductive frame 27 with fasteners such as screws 28 extending through holes 32 in base 30-A. The grounded apparatus will provide a ground to the frame 27 through the screws 28, the conductive base 30-A, the conductive body 30, the receptacles 2 through and the ground wire 3 to ground 4 (3 and 4 are not shown in this view)

Unlike the prior art, no snap is required to install the apparatus 100 according to the present invention, allowing the present invention to be installed essentially anywhere around the perimeter of the mat 1. Moreover, unlike the prior art the apparatus 100 does not require the drilling, cutting, or punching of holes in the mat 1, so there is no unused snap 6, 8 or holes 9, 9-A left in the previous location as seen in FIG. 1-C.

To install multiple Preferred Embodiments as shown FIG. 2-G, repeat the installation process as previously described. Although only four apparatii 100 are shown installed in FIG. 2-G, the maximum number would only be limited by the space allowed. Apparatus 100 on the back edge of mat 1 in the drawing is grounded by means of the banana plug 11, ground wire 3, and ground 4 and is providing the ground connection to the mat 1 as well due to being clamped to the mat 1 with its highly conductive bottom layer 1-B. The apparatus 100 on the front, right, and left are also grounded because all of the devices are attached to the mat and therefore electrically connected to the highly conductive bottom layer 1-B of the mat. If a direct path to ground 4 is desired, rather than through the bottom layer 1-B of the mat 1, install grounding wires 3 from the body 30 of the present invention directly to a ground 4 as shown in FIG. 2-F.

To remove apparatus 100 from a mat 1 and install it at a new location on the mat 1 or to move to a different mat 1, the tensioning screw 31 is loosened until the mat 1 may be easily removed from the slot 30-B. To ground an operator's ESD wrist strap 25, connect the banana plug 12 of an ESD wrist strap 25 into one of the receptacles 2 on a grounded Preferred Embodiment as shown in FIG. 2-F Description of a Second Illustrated Embodiment It will be appreciated that the apparatus 100 as described above may be formed in several different structural configurations. Several different embodiments are described below. A second illustrated embodiment of an apparatus 200 according to the present invention is shown in FIG. 3 through FIG. 3-C. As with the embodiment shown in FIG. 2, it can be constructed from any sufficiently strong and resilient conductive material such as carbon loaded ABS, nylon, zinc, or most any conductive material. Optionally, it can be made with an insulative material that is either coated with conductive material or has conductive material inserted to make the required connections. A material with a resistance of less than 20,000 ohms-cm is desirable.

Although the entire device can be conductive, the areas that are required to be conductive would be from each of the receptacles 2 to an L-shaped cantilever member 42 that is defined by an upwardly extending segment 43-A that is attached to the main body 46 and a cantilever free end 43-B that defines the base of apparatus 100 and which functions to clamp the mat 1 in a slot 45. The L-shaped cantilever member 42 thus has a first leg 43-B that is defined by the free end and a second leg 43-A that is attached to the main body 40. To have the optional snap 5 electrically connected to the base 42, the main body 40 and the cantilever screw 44 would require conductive material, coating, or inserts as well.

The main body 40 is shown with two receptacles 2 on each side, sized appropriately for a banana plug such as shown as 11 and 12. Slot 45 between the main body 40 and the cantilever base 43-A, as shown in FIG. 3-C, is used to receive a mat 1 in the same manner as described previously. A cantilever screw 44 is inserted through a hole in the segment 43-A and into a threaded hole in the main body 40 and defines the adjustment mechanism by which the apparatus is secured to a mat. As the cantilever screw 44 is tightened, the fixed end of the cantilever 43-A stops when it gets to the cantilever stop 41-A which causes the cantilever free end 43-B to move toward the cantilever body 40 and thereby secure the mat 1 and define an electrical pathway from the mat 1 through apparatus 200.

The cantilever 42 clamps the highly conductive bottom layer 1-B of mat 1 against the base 40 and provides a low resistance electrical connection between the bottom layer 1-B of the mat and the main body 40 and therefore to receptacles 2 in the body 40.

In addition to attaching to an ESD mat 1, auxiliary mounting holes such as holes 32 on the apparatus 100 described above could be added by increasing the width of the cantilever base 43 and adding holes. Because the base cantilever member 42 is electrically conductive and electrically connected to receptacles 2, this apparatus 200 can be grounded by attaching it to a grounded conductive frame 27 as shown in FIG. 2-H of a piece of equipment and, with the connection of a grounding wire 3, can provide a ground to a piece of equipment in a similar manner to that described above.

Operation of the Second Illustrated Embodiment

To install apparatus 200 onto a mat 1, an edge of a mat 1 is fit into slot 45 between the free end 43-B of cantilever member 42 as shown in FIG. 3-B. Cantilever screw 44 is then tightened. As described above, as the screw 44 is tightened the free end 43-B is urged against the mat 1—i.e., the width If slot 45 is decreased, thereby clamping the mat in the slot. No snap is required to install the apparatus 200, allowing the embodiment to be installed essentially anywhere around the perimeter of the mat 1.

To move apparatus 200 to a new location on the mat 1 or to move to a different mat 1, the cantilever screw 44 is loosed until the apparatus can be easily removed from the mat 1.

To ground a mat 1, a ground wire 3 is connected a receptacle 2 by means of banana plug 11 as described above and the other end of ground wire 3 is attached to common, electrical, or building ground 4.

Multiples of this embodiment 200 may be installed in a similar manner to the embodiment 100 described above, and providing a ground for an operator's ESD wrist strap 25 would be done in a similar manner to that described above.

Description of a Third Illustrated Embodiment

Yet another, third embodiment of an ESD grounding apparatus 300 is shown in FIG. 4 through FIG. 4-D. In this embodiment, as with prior embodiments, the main body 50 can be constructed from any sufficiently strong and resilient conductive material such as carbon loaded ABS, nylon, zinc, or most any conductive material. Optionally, the body 50 can be made with an insulative material that is either coated with conductive material or has conductive material inserted to make the required connections. A material with a resistance of less than 20,000 ohms-cm is desirable.

In apparatus 300 a spring clamp 52 is adapted to capture a main body 50 between opposed upper arm 57 and lower arm 59 of the spring clamp 42. The spring clamp is constructed of a resilient material such as spring steel. A handle 53 is attached to the terminal end of each of the upper and lower arms, 57 and 59, and may be constructed from a material such as carbon steel or any material with sufficient strength that the handles can open the spring clamp 52.

Although the entire apparatus 300 can be conductive, the areas that are required to be conductive would be from each of the receptacles 2 of main body 50 to the spring clamp 52.

The main body 50 is shown with two receptacles 2 on each side, sized appropriately for a banana plug such as shown as 11 and 12. The slot 58 between the main body 50 and the lower arm 59 of the spring clamp 52, as shown in FIG. 4 through 4-C, is used to receive and clamp apparatus 300 onto the mat 1. FIG. 4-C shows handles 53 rotated around the handle pivot 54 and used to open the spring clamp 52 by forcing the handles 53 together in the manner of a conventional binder clip. FIG. 4-B shows the apparatus 300 attached to a mat 1 with handles 53 in their relaxed position.

The spring clamp 52 clamps the highly conductive bottom layer 1-B of mat 1 against the main body 50 and provides a low resistance electrical connection between the bottom layer 1-B of the mat and the main body 50 and therefore to receptacles 2 in the main body 50.

In addition to attaching to an ESD mat 1, auxiliary mounting holes such as those on the previously described embodiments may be added by increasing the width of the at least the lower arm 59 of the spring clamp 52 and adding holes. Because the spring clamp 52 is electrically conductive and electrically connected to receptacles 2, this device can be grounded by attaching it to a grounded conductive frame 27 as shown in FIG. 2-H of a piece of equipment and, with the connection of a grounding wire 3, can provide a ground to equipment.

Operation of the Third Illustrated Embodiment

In a relaxed position the apparatus 300 is in the configuration shown in FIG. 4-D with the distal ends of the upper and lower arms 57 and 59 pressed together by the bias of the spring steel. To install apparatus 300 onto a mat 1, the handles 53 are moved to the position shown in FIG. 4-C and the handles 53 are squeezed together in the directions of arrows A to create a gap between the outer ends of upper and lower arms 57, 59. In this open position main body 50 and mat 1 may then be inserted into the slot 58 created by squeezing the handles 53. Pressure on the handles 53 is relaxed, which allows the spring clamp to capture and secure the mat 1 by virtue of the outer ends of the upper and lower arms being biased against the main body and mat. The handles may then be moved to the home or relaxed position as shown in FIG. 4-B (arrows B, FIG. 4-B).

To move apparatus 300 to a new location on the mat 1 or to move to a different mat 1, the handles 53 are moved to the position shown in FIG. 4-C and squeezed together to loosen the connection between apparatus 300 and mat 1 and main body 50, and to create a gap between the spring clamp 52 and the main body 50 and mat, the removing the mat 1.

To ground a mat 1, a ground wire 3 is inserted into a receptacle 2 by means of banana plug 11 with the opposite end of the ground wire 3 connected to common ground 4, which connects to electrical, or building ground.

Multiples of this apparatus 300 are installed in a similar manner to the preferred embodiment and providing a ground for an operator's ESD wrist strap would be done in a similar manner above.

Description of a Fourth Illustrated Embodiment

A fourth embodiment of an ESD grounding apparatus 400 is shown in FIG. 5 through FIG. 5-E. Apparatus 400 is comprised of a main body 60, which may be constructed from any sufficiently strong and resilient material, or optionally, fabricated from a conductive material such as carbon loaded ABS, nylon, zinc, or most any conductive material can be used, and a base 61, which is a resilient conductive material such as mild or spring steel. A handle 62 can be constructed from a material such as carbon steel, a plastic, or any material with sufficient strength that it can be used to secure the mat 1 without bending or breaking the handle.

Although the entire apparatus 400 can be conductive, the areas that are required to be conductive would be from each of the receptacles 2 to the base 61.

This embodiment is not shown with the optional snap 5, but one could be easily added with an adjustment of the size of either to the base 61 or to the body 60 to allow for the installation.

The main body 60 is shown with two receptacles 2 on each side, sized appropriately for a banana plug such as shown as 11 and 12. The slot 65 between the main body 60 and the base 61, as shown in FIGS. 5-A and 5-B, is used to receive and clamp the mat 1. FIG. 5-A shows handle 62 rotated to the open position to install or remove a mat 1—the handle is moved in the direction of arrow B to open the apparatus for insertion of a mat. FIG. 5-B shows the apparatus 400 attached to a mat 1 with lever 62 in the closed position, which secures the mat 1 between the lever nose 64-B and the base 61. To move the lever 62 into the closed position from the open position it is moved in the direction of arrow A, FIG. 5-B. It will be appreciated that the lever nose 64-B acts as a cam to bear down and apply pressure to the mat 1 in the slot 65 when the lever 62 is moved from the open to the closed position, thereby securing the mat in the slot.

The lever nose 64-B clamps the highly conductive bottom layer 1-B of mat 1 against the base 61, which provides a low resistance electrical connection between the bottom layer 1-B of the mat and the base 61 and therefore to the upper part of the base 61 and to the receptacles 2 in the body 60 in the same manner as detailed above with other alternatives.

Like other embodiments described herein, the embodiment shown in FIG. 5 through 5-E includes auxiliary mounting holes 32. Because the base 61 is electrically conductive and electrically connected to receptacles 2, this device can be grounded by attaching it to a grounded conductive frame 27 as shown in FIG. 2-H of a piece of equipment and, with the connection of a grounding wire 3, can provide a ground to equipment in a similar manner to the other alternative embodiments.

Operation of the Fourth Illustrated Embodiment

To install the apparatus 400 of the fourth embodiment onto a mat 1, the lever 62 is moved to the open position as shown in FIG. 5-A, which moves the lever nose 64-B so that the slot 65 is open. The mat 1 is slid into the slot 65 thus created and the lever 62 is rotated in the direction of arrow A in FIG. 5-B—i.e., the closed position—which causes lever nose 64-B to bear against mat 1, securing the mat in slot 65 and establishing the desired electrical continuity.

To remove the apparatus 400 from a mat 1, the lever 62 is rotated to the open position as shown in FIG. 5-A and the mat 1 is released from the engagement with the nose lever and may be removed.

To ground a mat 1, a ground wire 3 is inserted into a receptacle 2 by means of banana plug 11 and the other end of ground wire 3 to common ground 4, which connects to electrical, or building ground.

Multiples of this embodiment are installed in a similar manner to the embodiment described above and a ground for an operator's ESD wrist strap would be done in a similar manner to that already discussed.

As with the other embodiments, this embodiment would provide grounding points and provide a ground for ungrounded equipment in a similar manner to the embodiment shown in FIG. 2-H with the use of a ground wire 3.

Description of a Fifth Illustrated Embodiment

A final alternative embodiment of an apparatus 500 according to the invention is shown n in FIG. 6 through FIG. 6-C.

The base 71-A and 71-B is similar to the base 61 of the prior embodiment except that is has been bifurcated in order to allow a continuous ground monitoring system to test to see if a conductive mat is in place between the base left side 71-A and base right side 71-B, and that it is connected to ground 4.

If a shorting wire is connected between one of the receptacles on the left 72-A and receptacles on the right 72-B, this embodiment is essentially the same as the apparatus 400 of the prior embodiment.

The main body 70 should be made of insulative, rather than a conductive material.

This embodiment is not shown with the optional snap 5, but one could be easily added with an adjustment of the size of either to the base 71-A, 71-B, or both and could also be used for an auxiliary ground or for a connection to a ground monitoring system.

In contrast to apparatus 400, with the apparatus 500 the base is bifurcated into 71-A and 71-B, which makes receptacles 72-A and 72-B electrically isolated from one another.

Operation of the Fifth Illustrated Embodiment

The same method that is used with the apparatus 100 described above is used with apparatus 500 to install, remove, move, or ground apparatus.

To use the apparatus 500 as a mat 1 continuity monitoring connection device for ground a mat 1, install the apparatus to a mat 1 and attach a ground wire 3 into a receptacle 72-A by means of banana plug 11. Attach the other end of ground wire 3 to common ground 4. Attach a cable from the continuity test device to a receptacle 72-B on the other side. The testing device tests from receptacle 72-B through mat 1 to receptacle 72-A to ground 4.

Providing a ground for an operator's ESD wrist strap would be done in a similar manner to the preferred embodiment.

As with the other embodiments, this embodiment would provide grounding points and provide a ground for ungrounded equipment in a similar manner to the embodiment shown in FIG. 2-H with the use of a ground wire 3.

It will be evident from the foregoing description and drawings that there are numerous modifications that may be made to the ESD grounding apparatus of the invention that fall within the bounds of the invention. Such modifications may include, for example:

A. mounting a conventional snap to the body of any of the embodiments of an ESD grounding apparatus described herein so that the device may be used with conventional snap-to-wire connections;

B. use of other types of plugs and connectors instead of banana plugs in order to establish an electrical connection;

C. in addition to the embodiments specifically described above, other structural and functional approaches to attach the ESD grounding apparatus to a mat, including for example a magnetic attachment;

D. the ESD grounding apparatus defines a body that is clamped or otherwise attached to a mat and which established an electrical connection between a conductive layer in the mat and the body so that a grounding wire attached to the body grounds the mat. There are many different structures equivalent to those described above and shown in the drawings that are functionally equal;

E. with respect to the embodiment of FIGS. 5 through 5-E, there are some mats that have a multiple layers and where the highly conductive layer is internal to the mat and bounded by non-conductive layers on both sides. The apparatus 400 of FIG. 5 may be modified by inclusion of a conductive probe on the lever nose 64-B end of lever 64, which would be conductive, such that when the lever is moved into the closed position the probe penetrates the upper surface of the mat and makes electrical contact with the highly conductive, internal layer. This is shown schematically in FIG. 5-E with dashed line 64-C, which represents the probe. It will be appreciated that the same structure—a conductive probe—could be added to any of the ESD grounding apparatii described in the other embodiments described and shown herein. A small puncture in the mat caused by a conductive probe as described herein does not damage the mat because the small hole would be self-healing.

F. the use of securement members of a different structure from, for example, the threaded screw 31-A of FIG. 2, the cantilever arm 42 of FIG. 3, the clamp 52 of FIG. 4, the lever arm 62 of FIG. 5, all of which secure the body of the ESD grounding apparatus to the mat.

While the present invention has been described in terms of preferred and illustrated embodiments, it will be appreciated by those of ordinary skill that the spirit and scope of the invention is not limited to those embodiments, but extend to the various modifications and equivalents as defined in the appended claims.

The invention claimed is:

1. An electrostatic discharge(ESD) grounding apparatus for grounding a mat having an electrically conductive layer, the ESD grounding apparatus, comprising:
a body member adapted for removable attachment to the mat so that at least a portion of the body member is in direct electrical contact with the electrically conductive layer of the mat, the body member being defined by an upper body portion and a connected lower body portion and a slot therebetween, the slot having open opposed sides and an open front so that the slot is adapted for receiving the mat in the slot;
wherein the body member includes at least one receptacle for connecting a grounding wire to the body member and the grounding wire is electrically connected through an electrically conductive path to the portion of the body member that is in direct electrical contact with the electrically conductive layer of the mat.

2. The electrostatic discharge (ESD) grounding apparatus according to claim 1 wherein the lower body portion of the body member is defined by an L-shaped member that has an upwardly extending segment that is attached to the upper body portion and a free end that extends beneath the upper body portion to define the slot and the electrically conductive path extends through at least some of the free end.

3. The electrostatic discharge (ESD) grounding apparatus according to claim 2 including a securement member for securing the body member to the mat with the mat in the slot.

4. The electrostatic discharge (ESD) grounding apparatus according to claim 3 in which the lower body portion is in direct electrical contact with the electrically conductive layer of the mat and wherein the securement member is defined by a threaded screw that extends through a threaded bore in the upper portion so that the threaded screw may be tightened against and is in direct contact with the mat in the slot.

5. The electrostatic discharge (ESD) grounding apparatus according to claim 1 in which the body member defines the electrically conductive path and the body member may be attached to and removed from the mat without physically damaging the mat.

6. The ESD grounding apparatus according to claim 3 wherein the securement member is defined by a lever in the body member, the lever having a nose at one end thereof and movable between a first position in which the slot is unobstructed by the nose and a second position in which the nose obstructs the slot.

7. The ESD grounding apparatus according to claim 6 in which when a mat is in the slot and the lever is in the second position, the lever applies pressure to the mat to secure the mat in the slot.

8. The ESD grounding apparatus according to claim 3 wherein the securement member is defined by a cantilever member attached to the body member and having a free end that is spaced apart from the body member to define the slot.

9. The ESD grounding apparatus according to claim 8 in which the cantilever member is further defined by an L-shaped member in which a first leg defines the free end and a second leg is adjustably attached to the body member.

10. The ESD grounding apparatus according to claim 9 wherein the width of the slot is decreased by adjusting the attachment of the second leg to the body member and wherein the first leg is in electrical contact with the mat when the apparatus is attached to a mat.

11. The ESD grounding apparatus according to claim 3 wherein the securement member is defined by a clamp having an upper leg and a lower leg and wherein the body member is captured between upper leg and the lower leg and the slot is between the lower leg and a bottom surface of the body member.

12. The ESD grounding apparatus according to claim 11 wherein the clamp is movable from a relaxed position to an open position in which the upper leg and lower legs are separated and when in the open position the main body and the mat may be inserted between upper and lower legs.

13. An electrostatic discharge (ESD) grounding apparatus according for grounding a mat having an electrically conductive layer, the ESD grounding apparatus, comprising:
a body member adapted for removable attachment to the mat so that at least a portion of the body member is in direct electrical contact with the electrically conductive layer of the mat;
a body member attachment means for non-damaging attachment of the body member to the mat;
wherein the body member is a conductor defined by an upper body portion and a lower body portion electrically connected to the upper body portion and spaced apart therefrom by a slot that is adapted for insertion of a mat into the slot and so that the mat extends through the slot on opposite sides of the slot, and the body member includes at least one electrical receptacle for connecting a grounding wire to the body member and the electrical receptacle is electrically connected through the body member to the portion of the body member that is in direct electrical contact with the electrically conductive layer of the mat.

14. The electrostatic discharge (ESD) grounding apparatus according to claim 13 in which the body member attachment means further comprises the slot formed in the body member between the upper body portion and the lower body portion and in which the slot has open opposed sides and an open front, and including a mat securing member that applies pressure to the mat in the slot.

15. The electrostatic discharge (ESD) grounding apparatus according to claim 14 in which the mat securing member comprises a screw that extends through a bore in the upper portion so that the screw may be tightened against the mat in the slot and so that the screw is in direct contact with the mat.

16. The ESD grounding apparatus according to claim 14 in which mat securing member comprises a lever in the body member, the lever having a nose at one end thereof and movable between a first position in which the slot is unobstructed by the nose and a second position in which the nose applies pressure to the mat.

17. The ESD grounding apparatus according claim 16 including a probe on the nose and wherein the probe makes contact with the electrically conductive layer of the mat when the lever is in the second position.

18. The ESD grounding member according to claim 14 in which the body member attachment means further comprises an L-shaped cantilever having a first leg attached to the body member and having a free end defined by a second leg, wherein the slot is defined between the body member and the second leg.

* * * * *